(12) United States Patent  
Koyama

(10) Patent No.: US 11,291,414 B2
(45) Date of Patent: Apr. 5, 2022

(54) PATIENT MONITOR

(71) Applicant: NIHON KOHDEN CORPORATION, Tokyo (JP)

(72) Inventor: Yukio Koyama, Tokorozawa (JP)

(73) Assignee: NIHON KOHDEN CORPORATION, Tokyo (JP)

(*) Notice: Subject to any disclaimer, the term of this patent is extended or adjusted under 35 U.S.C. 154(b) by 0 days.

(21) Appl. No.: 16/359,144

(22) Filed: Mar. 20, 2019

(65) Prior Publication Data

US 2019/0290216 A1    Sep. 26, 2019

(30) Foreign Application Priority Data

Mar. 23, 2018    (JP) .............................. JP2018-055404

(51) Int. Cl.
| | |
|---|---|
| *A61B 5/00* | (2006.01) |
| *A61B 5/0205* | (2006.01) |
| *A61B 5/1455* | (2006.01) |
| *A61B 5/01* | (2006.01) |
| *A61B 5/021* | (2006.01) |
| *A61B 5/08* | (2006.01) |

(52) U.S. Cl.
CPC .............. *A61B 5/7405* (2013.01); *A61B 5/01* (2013.01); *A61B 5/02055* (2013.01); *A61B 5/14551* (2013.01); *A61B 5/742* (2013.01); *A61B 5/021* (2013.01); *A61B 5/0816* (2013.01)

(58) Field of Classification Search
CPC ..... A61B 5/7405; A61B 5/01; A61B 5/14551; A61B 5/02055; A61B 5/742; A61B 5/0816; A61B 5/021; A61B 5/746

See application file for complete search history.

(56) References Cited

U.S. PATENT DOCUMENTS

| | | | |
|---|---|---|---|
| 4,780,824 A | | 10/1988 | Niwa et al. |
| 5,253,645 A | * | 10/1993 | Friedman ........... A61B 5/02255 600/324 |
| 9,750,461 B1 | * | 9/2017 | Telfort ................. A61B 5/7221 |
| 2011/0080293 A1 | | 4/2011 | Tanishima et al. |
| 2011/0230729 A1 | * | 9/2011 | Shirasaki ........... A61B 5/02116 600/301 |
| 2014/0218198 A1 | | 8/2014 | Muneshima |
| 2014/0371546 A1 | | 12/2014 | Aoki et al. |

(Continued)

FOREIGN PATENT DOCUMENTS

| | | | | |
|---|---|---|---|---|
| GB | 2485690 A | * | 5/2012 | ........... A61B 5/7455 |
| JP | S62-155829 A | | 7/1987 | |

(Continued)

OTHER PUBLICATIONS

Japanese Office Action dated Nov. 16, 2021 issued in Japanese Patent Application No. 2018-055404.

*Primary Examiner* — James J Yang
(74) *Attorney, Agent, or Firm* — Pearne & Gordon LLP

(57) ABSTRACT

A patient monitor includes an interface configured to be connectable to a first sensor to measure first physiological information and to a second sensor to measure second physiological information, and a controller configured to actuate the second sensor to start a process for measuring the second physiological information in response to the first physiological information turning abnormal, the first physiological information being calculated based on a sensor signal acquired from the first sensor.

20 Claims, 6 Drawing Sheets

(56) References Cited

U.S. PATENT DOCUMENTS

| | | |
|---|---|---|
| 2016/0128634 A1 | 5/2016 | Kobayashi et al. |
| 2016/0183886 A1 | 6/2016 | Konno |
| 2019/0125212 A1 | 5/2019 | Maki et al. |

FOREIGN PATENT DOCUMENTS

| | | |
|---|---|---|
| JP | 2006-279796 A | 10/2006 |
| JP | 2009-039352 A | 2/2009 |
| JP | 2011-098189 A | 5/2011 |
| JP | 2014-147647 A | 8/2014 |
| JP | 2015-000110 A | 1/2015 |
| JP | 2015-058022 A | 3/2015 |
| JP | 2016-087326 A | 5/2016 |
| JP | 2016-122269 A | 7/2016 |
| WO | 2017/163938 A1 | 9/2017 |

* cited by examiner

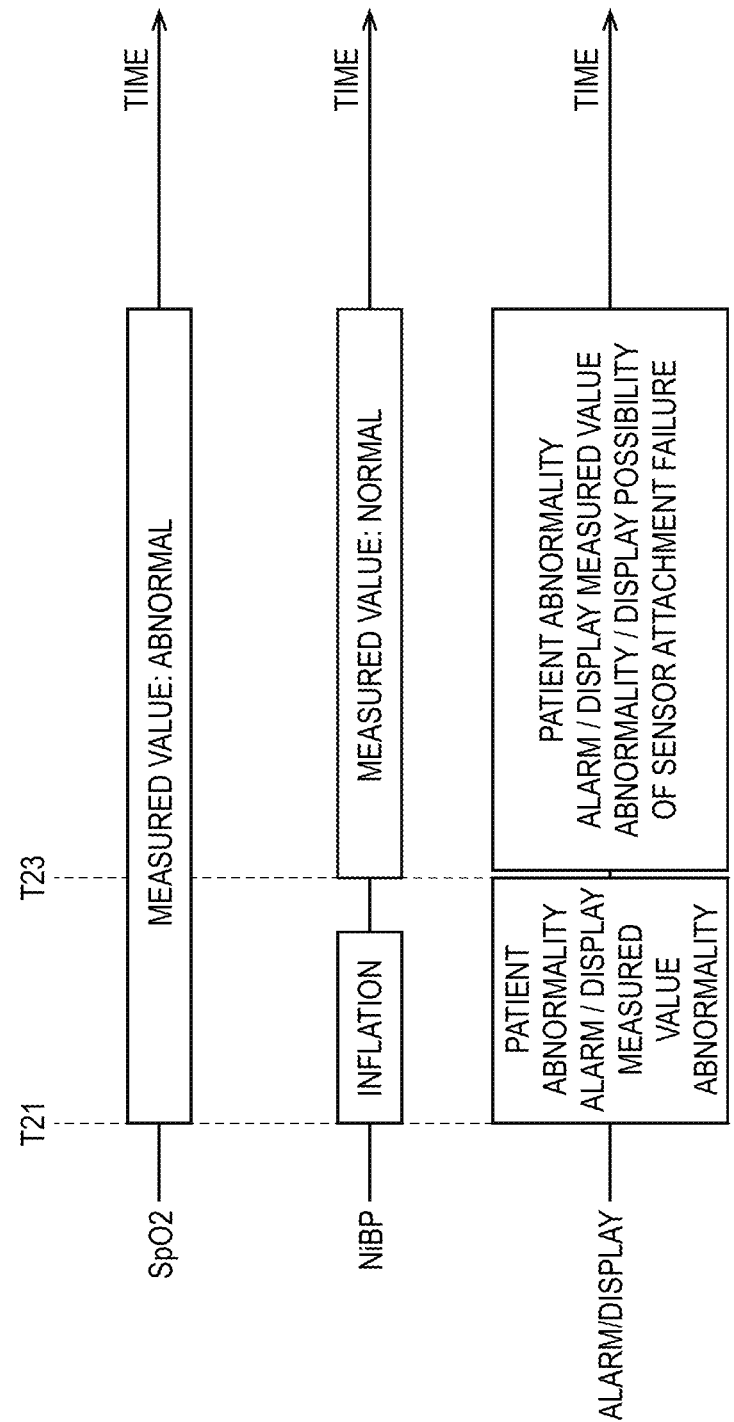

PATIENT MONITOR

CROSS-REFERENCE TO RELATED APPLICATION

The present application claims priority to Japanese Patent Application No. 2018-055404 filed on Mar. 23, 2018 the entire content of which is incorporated herein by reference.

BACKGROUND

The presently disclosed subject matter relates to a patient monitor.

Vital signs (such as blood pressure, a body temperature, respiration, pulse rate, arterial oxygen saturation) are used as information for monitoring a condition of a patient. A patient monitor calculates and displays measured values and waveforms of one or more vital signs such as (electrocardiogram, pulsation, respiration, body temperature) based on sensor signals acquired from various sensors (such as a cuff, electrocardiogram electrodes, a respiratory mask, and an SpO2 probe) attached to the patient. When there is an abnormality in the measured values and/or waveforms of the vital signs, the patient monitor outputs an alarm or a warning message. See, e.g., JP2015-000110A.

One or more sensors to be attached to a patient depends on a purpose of the measurement and a condition of the patient. For example, there may be a case where only an SpO2 (arterial oxygen saturation) probe is attached to a finger tip of the patient, and the patient monitor measures only the SpO2. In this case, if the patient suffers cardiac arrest, only a pulsation alarm or a probe confirmation alarm is generated. Same or similar alarm is generated also when a failure of attachment of an SpO2 probe occurs. Therefore, there may be a situation where it is difficult to determine whether the attachment the SpO2 probe is failed or the condition of the patient is suddenly changed.

That is, there has been a case where, when an abnormality occurs in a measured value or waveform of physiological information, a cause of the abnormality cannot clearly be determined.

This is not limited to the SpO2 measurement, but may be caused also in a case where other physiological information is measured.

SUMMARY

Illustrative aspects of the presently disclosed subject matter provide a patient monitor which, when an abnormality occurs in a measured value or waveform of physiological information, makes it easier for a user to determine a cause of the abnormality.

According an illustrative aspect of the presently disclosed subject matter, a patient monitor includes an interface configured to be connectable to a first sensor to measure first physiological information and to a second sensor to measure second physiological information, and a controller configured to actuate the second sensor to start a process for measuring the second physiological information in response to the first physiological information turning abnormal, the first physiological information being calculated based on a sensor signal acquired from the first sensor.

When the first physiological information turns abnormal, the controller actuates the second sensor to start the measurement of the second physiological information. Based on whether the second physiological information is normal or not, it becomes easier to determine whether there is an abnormality in a body condition of the patient or there is a failure in the attachment of the first sensor. That is, by referring to the second physiological information, the user can better understand what is occurring in the patient.

BRIEF DESCRIPTION OF DRAWINGS

FIG. 6 is a diagram illustrating another operation of the patient monitor.

DETAILED DESCRIPTION

Figure 1:
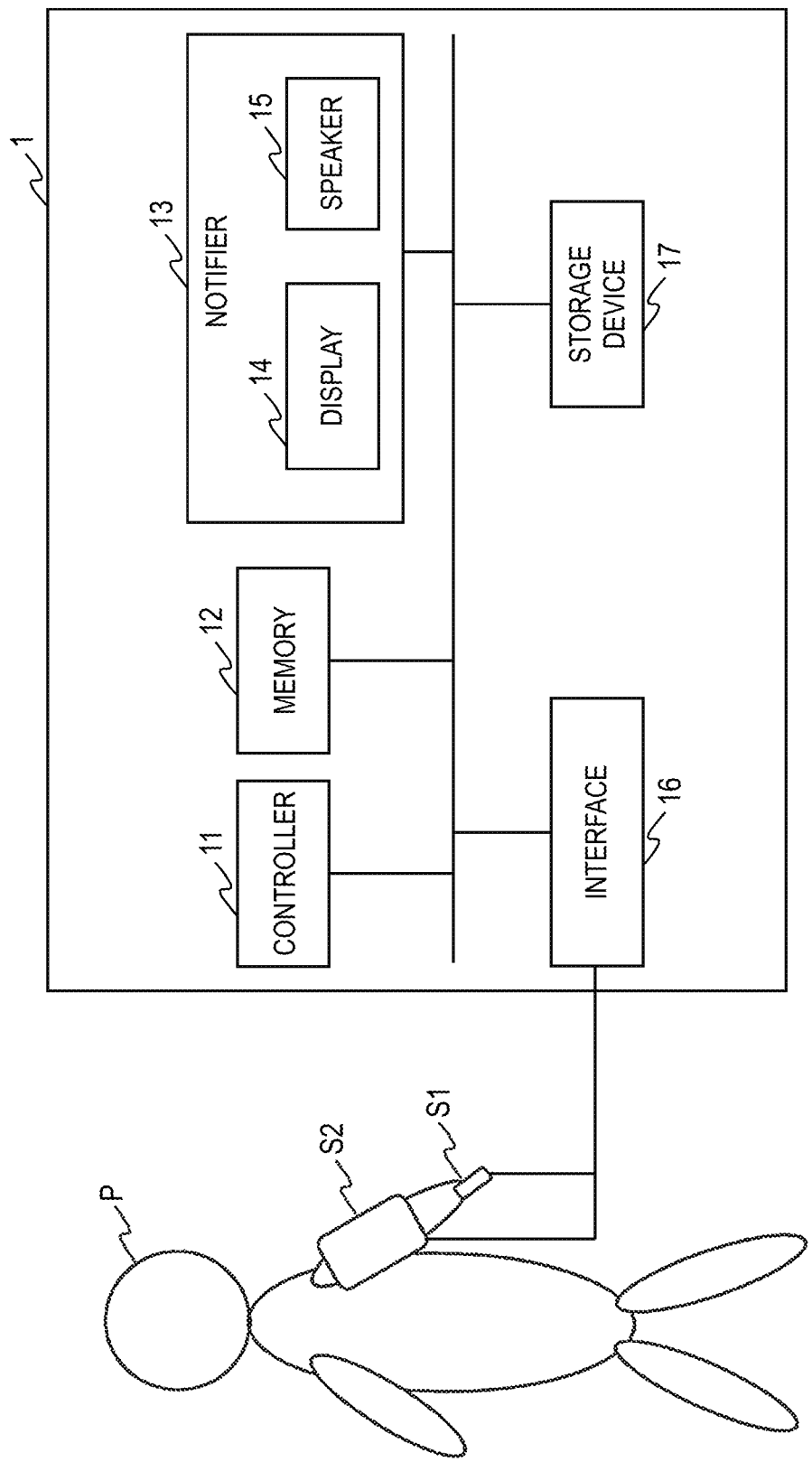
FIG. 1 is a block diagram illustrating a configuration of a patient monitor according to an embodiment of the presently disclosed subject matter.

Hereinafter, embodiments of the presently disclosed subject matter will be described with reference to the drawings. FIG. 1 is a block diagram illustrating a patient monitor 1 according to one embodiment of the presently disclosed subject matter. The patient monitor 1 is configured to receive sensor signals through various sensors (sensors S1, S2 which will be described later) connected (e.g., applied) to a patient P, and to acquire and display various items of physiological information (measured values and/or waveforms of vital signs) based on the sensor signals. The patient monitor 1 may include a connector insertion port to which connectors of the various sensors are to be connected. Here, the "physiological information" includes measured waveforms and measured values of the blood pressure, the SpO2 (arterial oxygen saturation), the respiration, the body temperature, the pulsation, and the like. The patient monitor 1 may be a bedside monitor or a medical telemeter to be carried by the patient P.

The sensors S1, S2 are connected (e.g., fixed by adhesion or wrapping) to the patient P to acquire various sensor signals of the patient. It is required that at least two or more sensors are connected to the patient P. Here, the first sensor S1 is preferably used for continuously measuring physiological information (first physiological information) of the patient P. The second sensor S2 is preferably used for intermittently measuring physiological information (second physiological information) of the patient P. Namely, the patient monitor 1 measures at least two kinds of physiological information (the first physiological information and the second physiological information). In the following example, the first physiological information is a measured value or a measured waveform of the SpO2, and the second physiological information is a blood pressure value measured by the non-invasive blood pressure (NiBP) measurement method.

In the following description, it is assumed that the sensor S1 (an example of a first sensor) is an SpO2 probe for measuring the SpO2, and the sensor S2 (an example of a second sensor) is a cuff for measuring the non-invasive blood pressure (NiBP). In the following description, it is further assumed that the SpO2 probe is attached to the fingertip of the patient P, and the cuff is attached to the upper arm of the patient P. Alternatively, other sensors such as electrodes for measuring an electrocardiogram, and a respiratory mask may be attached to the patient P. Although not illustrated, various configurations (such as a pressure sensor, a pump, and an electromagnetic valve) which are used for controlling the cuff may be appropriately disposed.

The patient monitor 1 may include a controller 11, a memory 12, a notifier 13, an interface 16, and a storage device 17. The notifier 13 may include a display 14 and a speaker 15. Although not illustrated, a user interface which is used for inputting an operation, and which is configured by buttons, knobs, and the like may be disposed in the patient monitor 1.

The display 14 is provided in the patient monitor 1, and is configured display measured waveforms and measured values of various items of physiological information under the control of the controller 11. The display 14 may be a so-called touch display. The speaker 15 outputs various alarm and operation sounds under the control of the controller 11.

For example, the memory 12 is a read only memory (ROM) or a random access memory (RAM). When the controller 11 executes a program, the memory 12 may function as a working area. Moreover, the memory 12 may store various programs which are to be executed by the controller 11.

The interface 16 receives a sensor signal which is acquired by the SpO2 probe, through a connector. After inflation by the cuff is caused, the interface 16 further receives a sensor signal (a pressure pulse wave of the cuff) for measuring the blood pressure, through a connector.

The interface 16 may wirelessly receive various sensor signals from the SpO2 probe and the cuff. In this case, the SpO2 probe and the cuff support various wireless communication standards, and the interface 16 receives sensor signals which are transmitted in accordance with the wireless communication standards. In the case where the wireless communication function is implemented in the interface 16, various data may be transmitted to and received from another device (such as a central monitor).

The storage device 17 is a secondary storage device which is disposed in the patient monitor 1, such as a hard disk drive. Alternatively, the storage device 17 may have a configuration which allows the storage device to be attachable to and detachable from the patient monitor 1. The controller 11 writes various data in the storage device 17, and reads data from the storage device 17 at a given timing. The storage device 17 stores programs which are to be executed by, for example, the controller 11.

The controller 11 controls the patient monitor 1. Generally, the process that is to be conducted by the controller 11 is implemented by an operation in which a processor, such as a central processing unit (CPU) or micro processing unit (MPU) reads a program from the memory 12 or the storage device 17, develops the program in the memory 12, and executes the developed program. A part of the process which is to be conducted by the controller 11 may be realized by various hardware resources (e.g., ASIC and FPGA circuits).

Here, the program may be stored in various types of non-transitory computer readable media, and then supplied to the computer (the patient monitor 1). The non-transitory computer readable medium includes tangible storage media of various types. Examples of the non-transitory computer readable medium include a magnetic recording medium (e.g., a flexible disk, a magnetic tape, and a hard disk drive), a magneto-optical recording medium (e.g., a magneto-optical disk), a Read only memory (CD-ROM), a CD-R, a CD-R/W, a semiconductor memory (e.g., a mask ROM, a programmable ROM (PROM), an erasable PROM (EPROM), a flash ROM, and a random access memory (RAM)). Alternatively, the program may be supplied to the computer by means of a transitory computer readable medium of any one of various types. Examples of the transitory computer readable medium include an electrical signal, an optical signal, and an electromagnetic wave. The transitory computer readable medium can supply the programs to the computer through a wired communication path such as an electric wire or an optical fiber, or a wireless communication path.

Hereinafter, the control performed by the controller 11 will be described in detail. The sensor signal acquired by the SpO2 probe is supplied to the controller 11 through the interface 16. By using a known algorithm, the controller 11 calculates the measured value or waveform of the SpO2 (an example of the first physiological information). The controller 11 causes the calculated value or waveform of the SpO2 to be displayed on the display 14. The controller 11 continuously performs the calculation process (in other words, constantly performs the process).

The controller 11 continuously determines whether the calculated measured value or measured waveform (the first physiological information) of the SpO2 is abnormal or not. This determination may be made by, for example, determining whether the measured value of the SpO2 is equal to or smaller than a threshold (e.g., 90%).

When the controller 11 detects that the measured value or measured waveform of the SpO2 has turned abnormal, the controller 11 outputs an alarm sound (an example of a first alarm sound) relating to a patient abnormality (an abnormality of the condition of the patient), through the speaker 15. In addition or alternatively, the controller 11 may cause a warning message relating to the SpO2 to be displayed on the display 14. The outputs of the alarm sound and the warning message in the case of an abnormality will be further described in detail with reference to FIGS. 3 to 6.

Usually, a non-invasive blood pressure measurement using a cuff involves compression, and therefore is not performed in a continuous manner, but performed in an intermittent manner. That is, while the cuff may be left attached to a patient, the inflation of the cuff is performed at a predetermined timing (e.g., only one every 30 minutes, or only at a timing when a medical person presses a measurement start button).

In such situation, when the controller 11 detects that the measured value or measured waveform of the SpO2 has turned abnormal, the controller 11 actuates the cuff (starts the inflation), and starts a process for measuring the non-invasive blood pressure. The controller 11 may start the inflation by transmitting a control signal for causing the air to flow into the cuff.

The controller 11 acquires the sensor signal relating to the blood pressure measurement from the cuff, and calculates blood pressure values (examples of the second physiological information, such as systolic blood pressure, mean blood pressure, and diastolic blood pressure) by using a known method. The controller 11 determines whether each of the blood pressures is abnormal or not. This determination may be made by comparing each of the blood pressures with a threshold.

When the controller 11 detects that not only the measured value or measured waveform (the first physiological information) of the SpO2 but also the blood pressure (the second physiological information) is abnormal, the controller 11 performs a notification (a display on the display 14, or an output of an alarm sound from the speaker 15) relating to the patient abnormality.

On the other hand, when it is detected that the measured value or measured waveform (the first physiological information) of the SpO2 is abnormal with the blood pressure (the second physiological information) not being abnormal, a notification (a display on the display 14, or an output of an alarm sound from the speaker 15) relating to an attachment failure of the SpO2 probe (the first sensor) is performed. The notification will be described in detail with reference to FIGS. 3 to 6. Examples of the "attachment failure" includes the SpO2 probe being completely dropped off, the SpO2 probe being displaced, a foreign substance existing between the SpO2 probe and the human body, and the like.

When the measured value or waveform becomes abnormal for the continuously measured SpO2, it is difficult to clearly determine whether the condition of the patient has suddenly changed or whether an attachment failure has occurred such as dropping off of a probe. However, with the configuration described above, when the controller 11 detects that the measured value or measured waveform (the first physiological information) of the SpO2 is abnormal, the controller 11 actuates the cuff (the second sensor) which has been stopped, to start the measurement of the blood pressure (the second physiological information). Both the SpO2 (arterial oxygen saturation) and the blood pressure are indexes indicating the normality of the circulatory system of the patient P. Therefore, when the blood pressure is also abnormal, it is likely that the condition of the patient has suddenly changed, and when the blood pressure is normal, it is likely that there is an attachment failure of the SpO2 probe (the first sensor). By actuating the cuff (the second sensor) as described above, it is possible to better determine the condition of the patient.

Figure 2:
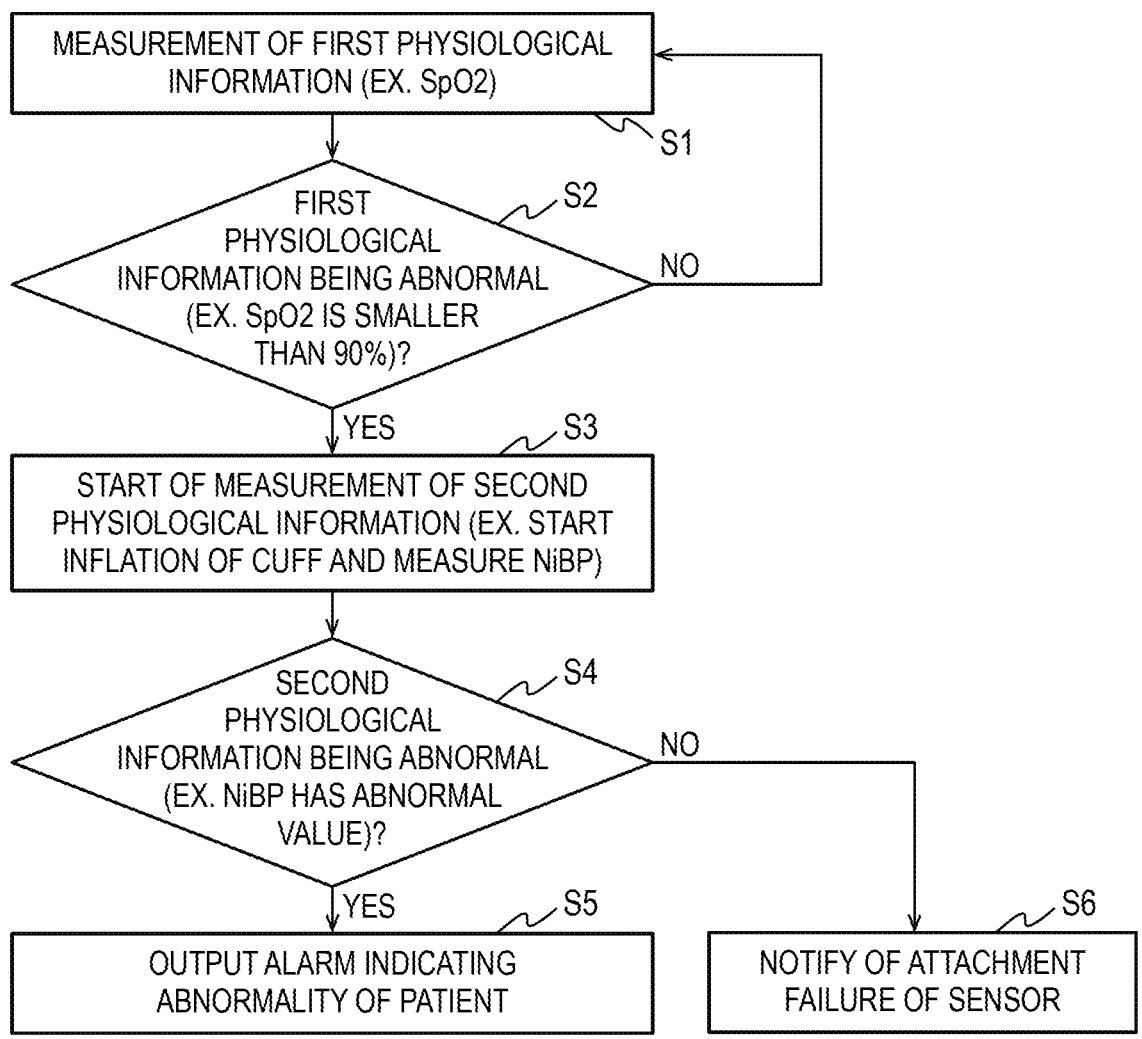
FIG. 2 is a flowchart illustrating an example of an operation of the patient monitor.

Next, the operation of the patient monitor 1 according to an embodiment of the presently disclosed subject matter will be further described with reference to the flowchart of FIG. 2. The controller 11 receives the sensor signal relating to the SpO2, from the SpO2 probe. The controller 11 calculates the measured value or measured waveform of the SpO2 based on the sensor signal (S1). The controller 11 determines whether the measured value or measured waveform of the SpO2 is abnormal or not (S2). In the example of FIG. 2, if the measured value (the first physiological information) of the SpO2 becomes smaller than 90%, it is determined that the measured value or measured waveform of the SpO2 has turned abnormal (S2).

The controller 11 compares the measured value of the SpO2 with the threshold (90%). If the measured value/measured waveform of the SpO2 is not abnormal (S2: No), the controller 11 continuously measures the SpO2 (S1).

When the measured value of the SpO2 becomes abnormal (S2: Yes), the controller 11 starts actuating the cuff (the sensor S2) to start the measurement of the non-invasive blood pressure (NiBP) (S3). At this timing, the controller 11 may output an alarm for the patient abnormality. Thereafter, the controller 11 determines whether the blood pressure is abnormal or not. Also this determination may be performed by, for example, comparing the threshold with the measured value.

When the blood pressure is abnormal (S4: Yes), the controller 11 determines that an abnormality derived from the body of the patient occurs, and outputs an alarm (S5). In addition to the output of the alarm, the controller 11 may cause information indicating an abnormality of the body condition of the patient, to be displayed on the display 14.

When the blood pressure is normal (S4: No) on the other hand, there is a possibility that the measured value or measured waveform of the SpO2 is made abnormal by a failure of the attachment of the SpO2 probe. In this case, the controller 11 notifies of the possibility of an attachment failure of the SpO2 probe, through the notifier 13 (S6). Variations of the notification will be described with reference to FIGS. 3 to 6.

Then, variations of the alarm output and display control of the patient monitor 1 will be described with reference to FIGS. 3 to 6.

Figure 3:
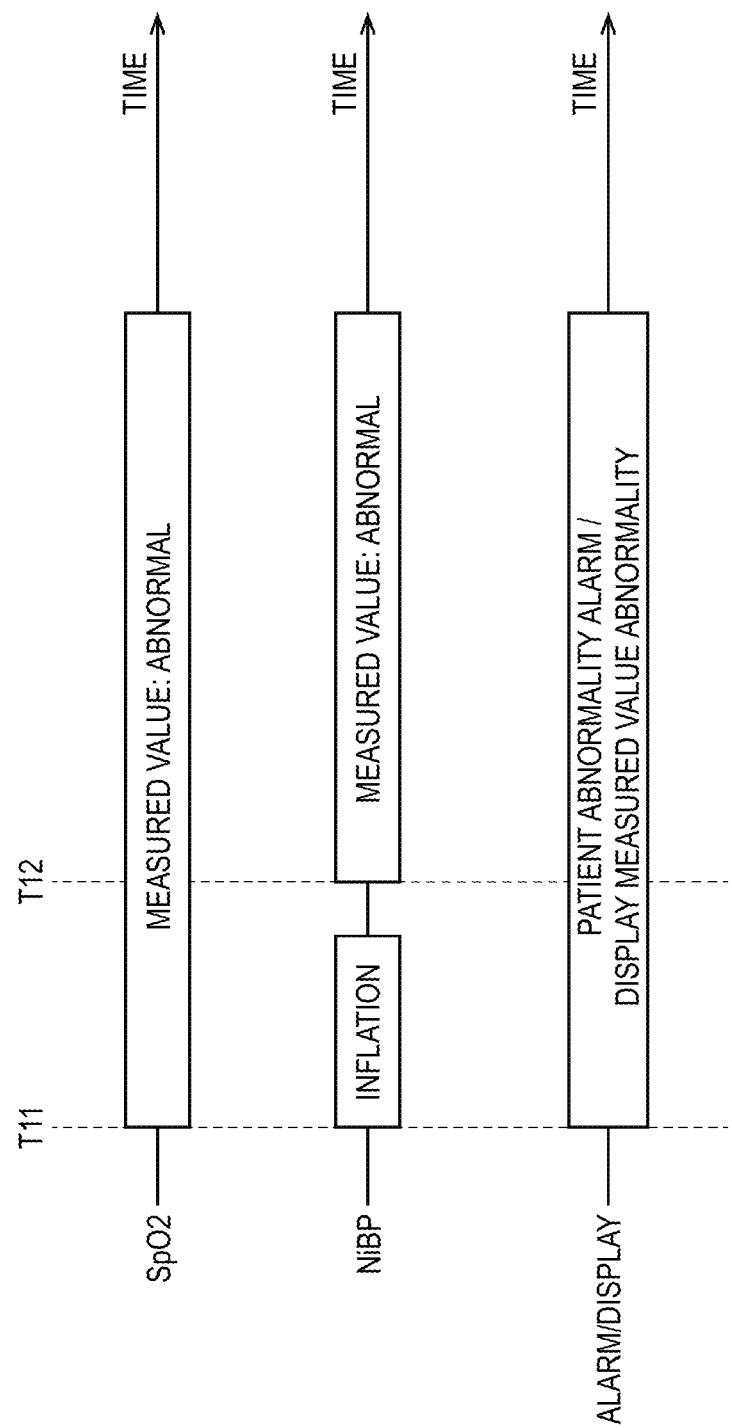
FIG. 3 is a diagram illustrating an operation of the patient monitor.

First, the alarm output and display in the case where both the SpO2 and the blood pressure (the non-invasive blood pressure) are abnormal will be described with reference to FIGS. 3 and 4. FIG. 3 is a conceptual diagram illustrating a first operation example of the patient monitor 1. As described with reference to FIG. 2, the controller 11 continuously calculates the measured value or measured waveform of the SpO2. In the following description referring to FIGS. 3 to 6, it is assumed that only the measured value of the SpO2 is considered. With respect to the blood pressure, same or similarly, it is assumed that only the measured value is considered, and the measured waveform is not considered. In the following description, namely, the first physiological information is assumed to be the measured value of the SpO2, and the second physiological information is assumed to be the blood pressure which is acquired by the non-invasive method.

When the controller 11 detects an abnormality of the measured value of the SpO2 at timing T11, in response to this, the controller 11 starts actuating the cuff (the sensor S2) to start the measurement of the non-invasive blood pressure (T11). Moreover, the controller 11 outputs an alarm indicating that the measured value of the SpO2 is abnormal, through the speaker 15, and causes a message or the like informing of the abnormality of the measured value of the SpO2 to be displayed on the display 14 (T11).

After the inflation by the cuff is ended, the controller 11 starts the measurement of the blood pressure, and determines whether the blood pressure is abnormal or not. At timing T12, the controller 11 detects that the blood pressure is abnormal. In response to this, the controller 11 continuously outputs an alarm indicating the patient abnormality, and causes information indicating that both the blood pressure and the measured value of the SpO2 are abnormal, to be displayed on the display 14.

Figure 4:
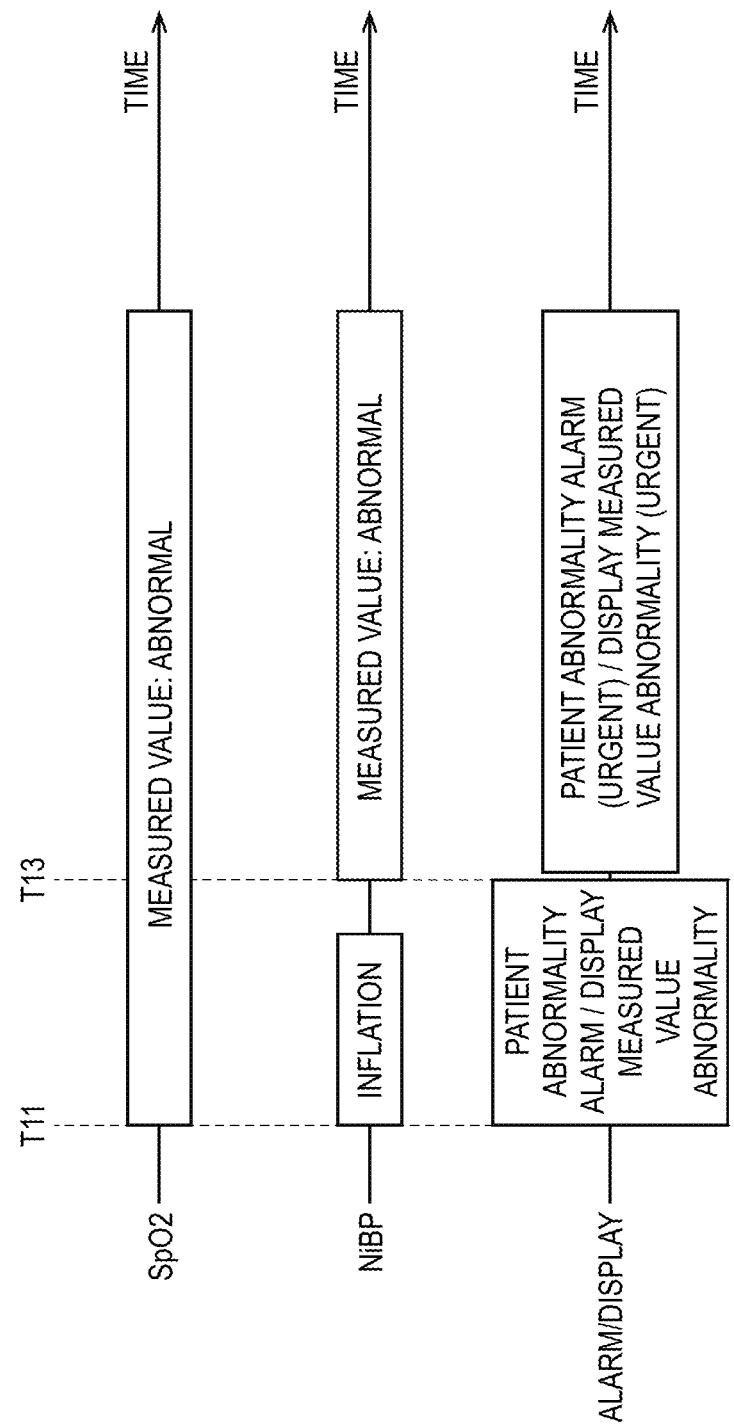
FIG. 4 is a diagram illustrating another operation of the patient monitor.

FIG. 4 is a conceptual diagram illustrating a modification of the operation example of FIG. 3. The operations which are conducted until timing T11 are identical with those illustrated in FIG. 3. At timing T13, the controller 11 detects that, in addition to the measured value of the SpO2, the blood pressure is abnormal. In this case, it is very likely that a serious abnormality is occurring in the circulatory system of the patient. At timing T13, therefore, the controller 11 switches the alarm sound to another alarm sound having a different tone (an example of a second alarm sound indicating the patient abnormality) to indicate a higher urgency, thereby notifying of an urgent situation. Alternatively, the controller 11 may notify of an urgent situation by raising the volume level of the alarm or causing a display indicating the urgency to be displayed on the display 14. By raising the degree of urgency or volume level of the alarm when it is detected that not only the first physiological information (the measured value of the SpO2) but also the second physiological information (the blood pressure) is abnormal as described above, a medical person can be informed of the possibility of a highly urgent situation more quickly, and a speedy countermeasure can be promoted.

Then, the alarm output and display in the case where only the SpO2 is abnormal will be described with reference to FIGS. 5 and 6. First, FIG. 5 will be referred. It is assumed that the controller 11 detects at timing T21 that the measured value of the SpO2 is abnormal. In response to this, the controller 11 starts actuating the cuff (the sensor S2) to start the measurement of the non-invasive blood pressure (T21). Moreover, the controller 11 outputs the alarm notifying that the measured value of the SpO2 is abnormal, through the speaker 15, and causes the display indicating the abnormality of the measured value to be displayed on the display 14 (T21).

At timing T22, the controller 11 detects that the blood pressure is normal. Namely, the controller 11 detects that the measured value of the SpO2 is abnormal, but the blood pressure is normal. In this case, it is possible that the cause is only the non-attachment of the SpO2 probe. Therefore, the controller 11 visually indicates on the display 14 that the measured value of the SpO2 is abnormal, stops the alarm indicating the patient abnormality, and starts an output of a technical alarm (an example of a third alarm sound) indicating the attachment failure of the SpO2 probe (T22). Alternatively, the controller 11 may cause a display indicating the attachment failure of the SpO2 probe, to be displayed on the display. When the technical alarm is output as described above, the medical person can be more clearly informed of the situation where it is likely that there is an attachment failure of the SpO2 probe. Therefore, the medical person (the doctor, the nurse, or the like) can promptly take an adequate countermeasure such as reattaching of the SpO2 probe.

Figure 5:
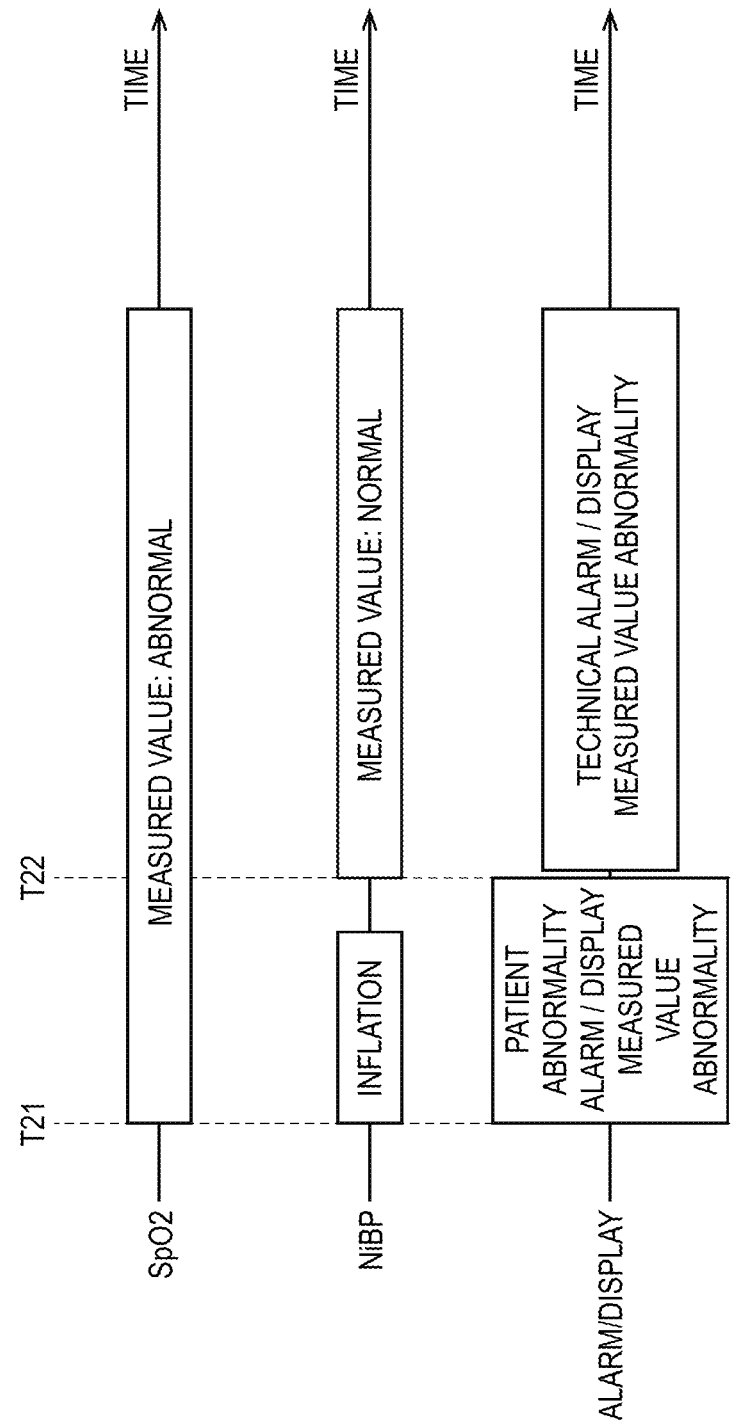
FIG. 5 is a diagram illustrating another operation of the patient monitor.

FIG. 6 is a conceptual diagram illustrating a modification of the operation example of FIG. 5. The operations which are conducted until timing T21 are identical with those illustrated in FIG. 5. At timing T23, the controller 11 detects that the measured value of the SpO2 is abnormal, but the blood pressure is normal. In this case, the only cause may be a non-attachment of the SpO2 probe, but it cannot be denied that an abnormality is occurring in the body condition of the patient. Therefore, the controller 11 continues to output the alarm indicating the patient abnormality, causes the abnormality of the measured value of the SpO2 to be displayed on the display 14, and causes a message suggesting the possibility that detachment of the SpO2 probe merely occurs, to be displayed on the display 14 (T23).

The operations of FIGS. 5 and 6 are mere examples. When the measured value of the SpO2 is abnormal with the blood pressure (the non-invasive blood pressure) being normal, the controller 11 may notify of the possibility of the attachment failure of the SpO2 probe by any means using, for example, a sound or a display. Alternatively, the controller 11 may control a communication mechanism of the interface 16, and transmit a message (an e-mail or the like) indicating the possibility of the attachment failure of the SpO2 probe, to another device (e.g., a terminal device carried by the nurse), thereby performing the notification.

In the examples of FIGS. 3 to 6, an alarm is output at a timing when the measured value of the SpO2 turns abnormal. In another example, the controller 11 may output an alarm only after both the measured value of the SpO2 and the blood pressure value are detected. For example, the controller 11 may output the alarm indicating the patient abnormality, and perform the display indicating the patient abnormality, only after both the measured value of the SpO2 and the blood pressure turns abnormal. The controller 11 may start processes such as the output of the alarm (e.g., the output of the technical alarm, the output of the alarm indicating the patient abnormality, and the display indicating the attachment failure of the SpO2 probe), only after it is detected that the measured value of the SpO2 is abnormal with the blood pressure being normal.

According to the patient monitor 1 described above, the controller 11 actuates the second sensor (e.g., the cuff for measuring the NiBP) to start measuring the second physiological information (e.g., the non-invasive blood pressure) in response to the first physiological information (e.g., the measured value or waveform of the SpO2) turning abnormal. Based on whether the second physiological information is normal or not, it becomes easier to determine whether there is an abnormality in the body condition of the patient or there is a failure of an attachment of the first sensor (e.g., the SpO2 probe). That is, by referring to the second physiological information, it is possible to better understand the situation of the patient.

While the presently disclosed subject matter has been described with reference to a certain embodiment thereof for facilitating understanding of the presently disclosed subject matter, the scope of the presently disclosed subject matter n is not limited to the embodiments described above, and it will be understood by those skilled in the art that various changes and modifications may be made therein without departing from the scope as defined by the appended claims.

In a non-invasive blood pressure measurement using a cuff, for example, the linear inflation measurement method (the method in which the blood pressure is measured during inflation) may be used instead of the deflation measurement.

The first physiological information is not limited to the measured value or measured waveform of the SpO2 as described above, and may be a respiration rate/respiratory waveform, a pulse rate, a body temperature, and the like. The second physiological information is not always limited to the non-invasive blood pressure, and, for example, may be information relating to the blood refill time (see, e.g., JP2016-087326A). That is, the second physiological information may be calculated by a measurement method involving, for example, compression.

In the above example, the second sensor is actuated in response to the first physiological information (in the examples of FIGS. 3 to 6, the measured value of the SpO2) turning abnormal. The presently disclosed subject matter is not limited to this. According to another embodiment of the presently disclosed subject matter, the controller 11 may actuate the second sensor in response to the sensor signal acquired from the first sensor turning abnormal.

The sensor signal being abnormal includes, for example, a case where an instantaneous interruption of the sensor signal acquired from the first sensor is repeated (e.g., a case where the number of instantaneous interruptions within a predetermined period of time is equal to or larger than a threshold), and a case where the sensor signal acquired from the first sensor contains a noise equal to or higher than a predetermined level. The interface 16 may have a typical noise detection mechanism or signal level detection mechanism to detect the abnormality.

The controller 11 may activate the second sensor (the cuff), and perform various alarm output and display controls illustrated in FIGS. 3 to 6 in response to the sensor signal acquired from the first sensor turning abnormal. When the sensor signal acquired from the first sensor is abnormal with the second physiological information being normal, for example, the controller 11 performs a notification relating to the attachment failure of the first sensor (e.g., an output of a technical alarm such as illustrated in FIG. 5, or a display indicating an attachment failure such as illustrated in FIG. 6). When the sensor signal acquired from the first sensor is abnormal and the second physiological information is also abnormal, the controller 11 may change the normal alarm to an alarm of the urgency level or raise the volume level of the alarm as indicated in FIG. 4.

According to another embodiment of the presently disclosed subject matter, the patient monitor 1 may be configured to start actuating a sensor associated with physiological information for which a measurement has been stopped, when only one of the measured physiological information (e.g., the respiration rate and the SpO2) becomes abnormal. This will be described below in detail.

A plurality of sensors (in the following example, a mask for respiration measurement and an SpO2 probe) are attached to the patient P. The interface 16 is configured to be connectable to the plurality of sensors. Sensor signals relating to the respiration, and those relating to the SpO2 are supplied to the controller 11 through the interface 16. The controller 11 measures a plurality of items of physiological information from these multiple kinds of sensor signals. In the example, the controller 11 calculates the physiological information (e.g., the respiration rate and the respiratory waveform) relating to the respiration, and the physiological information (the measured value, the measured waveform) relating to the SpO2, and continuously determines whether each physiological information is abnormal or not.

In response to only one or some of the plurality of items of physiological information turning abnormal (e.g., when only the measured value of the SpO2 becomes abnormal with the respiration rate and the like being normal), the controller 11 actuates a sensor (e.g., a cuff) which has been in a non-operating state to start the measurement of another one of the plurality of items of physiological information (e.g., the non-invasion blood pressure). When all the items of physiological information (e.g., the respiration and the SpO2) turn abnormal, the controller 11 outputs the alarm indicative of a patient abnormality.

When the condition of the patient is suddenly changed, the sudden change is caused by an abnormality of the circulatory system in many cases, and the abnormality of the circulatory system causes abnormalities in other items of physiological information in many cases. On the other hand, when only one item of physiological information is abnormal, it is likely that there is an attachment failure (contact failure) of the sensor. Therefore, when only one or some of the plurality of items of physiological information becomes abnormal, it becomes easier to better understand the condition of the patient in detail by measuring the physiological information that has not been measured.

What is claimed is:

1. A patient monitor comprising:
    an interface configured to be connectable to a first sensor to measure first physiological information and to a second sensor to measure second physiological information being different from the first physiological information; and
    a controller configured to,
    in response to the first physiological information turning to a first abnormal state;
        start an output of a patient abnormality alarm;
        actuate the second sensor to obtain the second physiological information from the second sensor to determine a cause of the first abnormal state of the first physiological information;
        determine that an attachment failure of the first sensor has occurred and stop the output of the patient abnormality alarm when the second physiological information of the actuated second sensor does not indicate a second abnormal state and the first physiological information has turned to the first abnormal state; and
        determine that a patient is in an abnormal condition and notify the abnormal condition of the patient when the second physiological information of the actuated second sensor indicates the second abnormal state and the first physiological information has turned to the first abnormal state.

2. The patient monitor according to claim 1, wherein the first physiological information is continuously measured, and the second physiological information is intermittently measured.

3. The patient monitor according to claim 1, wherein the controller is configured to start an output of a first alarm sound in response to the first physiological information turning abnormal, and to raise a volume level of the alarm sound or to output a second alarm sound having a different tone from the first alarm sound after the controller has determined that the second physiological information is also abnormal.

4. The patient monitor according to claim 1, wherein the controller is configured to perform a notification relating to an attachment failure of the first sensor when the second physiological information is normal with the first physiological information being abnormal.

5. The patient monitor according to claim 4, wherein the controller is configured to output a third alarm sound when the second physiological information is normal with the first physiological information being abnormal.

6. The patient monitor according to claim 4, wherein the controller is configured to output a first alarm sound and to perform a display relating to the attachment failure of the first sensor when the second physiological information is normal with the first physiological information being abnormal.

7. The patient monitor according to claim 1, wherein the controller is configured to start an output a first alarm sound only after the controller detects both an abnormality of the first physiological information and an abnormality of the second physiological information.

8. The patient monitor according to claim 1, wherein the first physiological information includes at least one of an arterial oxygen saturation, a respiration rate, a respiratory waveform, a pulse rate and a body temperature, and
    wherein the second physiological information includes one of a non-invasive blood pressure and a blood refill time.

9. The patient monitor according to claim 1, wherein the second physiological information includes a non-invasive blood pressure.

10. A patient monitor comprising:
    an interface configured to be connectable to a first sensor for measuring first physiological information and to a second sensor for measuring second physiological information being different from the first physiological information; and
    a controller configured to,
    in response to detecting a repetition of an instantaneous interruption of a sensor signal acquired from the first sensor;
        start an output of a patient abnormality alarm;
        actuate the second sensor to obtain the second physiological information from the second sensor to determine a cause of the instantaneous interruption of the sensor signal;

determine that an attachment failure of the first sensor has occurred and stop the output of the patient abnormality alarm when the second physiological information of the actuated second sensor indicates a normal state, and the repetition of an instantaneous interruption of a sensor signal has been acquired from the first sensor; and determine that a patient is in an abnormal condition and notify the abnormal condition of the patient when the second physiological information of the actuated second sensor indicates an abnormal state and the repetition of an instantaneous interruption of a sensor signal has been acquired from the first sensor.

11. The patient monitor according to claim 10, wherein the controller is configured to perform a notification relating to an attachment failure of the first sensor when the second physiological information is normal with the sensor signal being abnormal.

12. The patient monitor according to claim 10, wherein the controller is configured to start to output a first alarm sound in response to the sensor signal turning abnormal, and to raise a volume level of the first alarm sound or to output a second alarm sound having a different tone from the first alarm sound after the controller has determined that the second physiological information is also abnormal.

13. The patient monitor according to claim 10, wherein the first physiological information includes at least one of an arterial oxygen saturation, a respiration rate, a respiratory waveform, a pulse rate and a body temperature, and wherein the second physiological information includes one of a non-invasive blood pressure and a blood refill time.

14. A patient monitor comprising:

an interface configured to be connectable to a plurality of sensors; and a controller configured to obtain a plurality of items of physiological information including first physiological information from a first sensor and second physiological information from a second sensor, the second physiological information being different from the first physiological information, and in response to the first physiological information turning to be a first abnormal state and the second physiological information indicating a first normal state:

start an output of a patient abnormality alarm;

actuate one of the plurality of sensors which has been in a non-operating state to start a measurement to obtain third physiological information to determine a cause of the first abnormal state of the first physiological information;

determine that an attachment failure of the first sensor has occurred and stop the output of the patient abnormality alarm when the third physiological information indicates a second normal state, and the first physiological information has turned to be the first abnormal state; and determine that an abnormality of a circulatory system of a patient has occurred when the third physiological information indicates a second abnormal state, and the first physiological information has turned to be the first abnormal state.

15. The patient monitor according to claim 14, wherein the first physiological information includes at least one of an arterial oxygen saturation, a respiration rate, a respiratory waveform, a pulse rate and a body temperature, and wherein the second physiological information includes one of a non-invasive blood pressure and a blood refill time.

16. A patient monitor comprising:

an interface configured to be connectable to a first sensor for measuring first physiological information and to a second sensor for measuring second physiological information being different from the first physiological information; and a controller configured to, in response to a sensor signal acquired from the first sensor turning to a first abnormal state:

start an output of a patient abnormality alarm;

actuate the second sensor to obtain the second physiological information from the second sensor to determine a cause of the first abnormal state of the first sensor;

determine that an attachment failure of the first sensor has occurred and stop the output of the patient abnormality alarm when the second physiological information of the actuated second sensor does not indicate a second abnormal state, and the sensor signal acquired from the first sensor has turned to the first abnormal state; and determine that a patient is in an abnormal condition when the second physiological information of the actuated second sensor indicates the second abnormal state, and the sensor signal acquired from the first sensor has turned to the first abnormal state.

17. The patient monitor according to claim 16, wherein the first physiological information includes at least one of an arterial oxygen saturation, a respiration rate, a respiratory waveform, a pulse rate and a body temperature, and wherein the second physiological information includes one of a non-invasive blood pressure and a blood refill time.

18. The patient monitor according to claim 1, wherein the controller is further configured to output a first alarm to warn the attachment failure of the first sensor when the second physiological information of the actuated second sensor is not abnormal and a second alarm to warn the abnormal condition of the patient when the second physiological information of the actuated second sensor indicates the abnormal state.

19. The patient monitor according to claim 1, wherein in response to determining that the patient is in the abnormal condition, the controller is further configured to switch the patient abnormality alarm into another alarm sound having a different tone to indicate a higher urgency.

20. The patient monitor according to claim 10, wherein in response to determining that the patient is in the abnormal condition, the controller is further configured to switch the patient abnormality alarm into another alarm sound having a different tone to indicate a higher urgency.

* * * * *